United States Patent [19]

Minson

[11] Patent Number: 5,045,447
[45] Date of Patent: Sep. 3, 1991

[54] METHOD OF PRODUCING ANTIBODIES TO HPV

[76] Inventor: Anthony C. Minson, 113 Cambridge Road, Great Shelford, Cambridge, England

[21] Appl. No.: 323,682

[22] Filed: Mar. 15, 1989

[51] Int. Cl.[5] ..................... C12Q 1/02; G01N 33/569
[52] U.S. Cl. ...................................... 435/5; 435/7.92; 436/548; 935/110; 422/61
[58] Field of Search ............................... 436/547, 548; 435/172.2; 935/22, 23, 32

[56] References Cited

U.S. PATENT DOCUMENTS 4,777,239 10/1988 Schoolnik et al. .................. 530/326

FOREIGN PATENT DOCUMENTS 242243 6/1987 European Pat. Off. .

OTHER PUBLICATIONS

Banks, et al., J. Gen. Virol., 68, pp. 3081–3089, 1987.
U.S. Ser. No. 58,387, 7/43, H. V. Gelbain, et al., abstract only.
Browne, et al., J. Gen. Virol., 69, pp. 1263–1273, 1988.
Doorbar, et al., J. Virol., 61(9), 2793–2799, 1987.
Kieng, et al., Biotechnology, vol. 4, 790–795, 1986.
Chakrabarti, et al., Nature, vol. 320, 535–537, 1986.
J. C. Sterling, et al., J. Cell Biochem. Supplement, No. 13, Part C, Dec. 1989 (U.S.).
J. C. Sterling, et al., New Mexico Symposium on Papillomaviruses, Mar. 11–18, 1989.
Shepherd BSI Abstract, Nov. 1988.
D. Espion, et al., Arch. Virol., 1987, 95 (1–2), pp. 79–95, abstract only.
Doorbar, et al., Embo. J., 8(3), p. 825 (1988).
Schneider-Gadicke, Cancer Res. (1988) 48, 2969–2974.
Ottersdorf, J. Gen. Virol. (1987) 68, 2933.

Primary Examiner—Christine Nucker
Assistant Examiner—Jeffrey Stucker
Attorney, Agent, or Firm—Walter H. Dreger

[57] ABSTRACT

A method for the production of antibodies to an immunogen, wherein hybridoma culture supernatants are screened using cells infected with a virus recombinant encoding one or more epitopes of the immunogen.

The method disclosed is particularly advantageous as: 1) cells infected with the virus recombinant can provide a good supply of an antigen; 2) the antigen is expressed in a mammalian cell and it is therefore synthesized and processed in a form essentially identical to the antigen found in a natural infection; and 3) the infected cells may be subjected to the same pre-treatments as applied to test sample tissues before their use in the hybridoma screening procedure. This ensures that the antibodies selected will recognize epitopes resistant to these pre-treatments and which may therefore be expected to be present on the test samples as prepared for analysis.

17 Claims, 7 Drawing Sheets

Fig. 1.
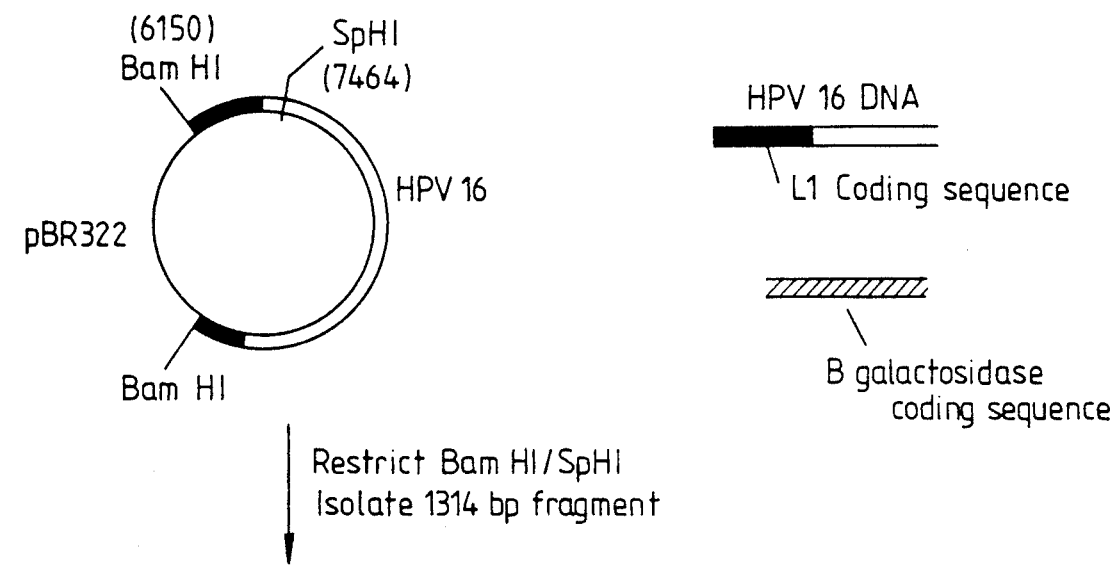
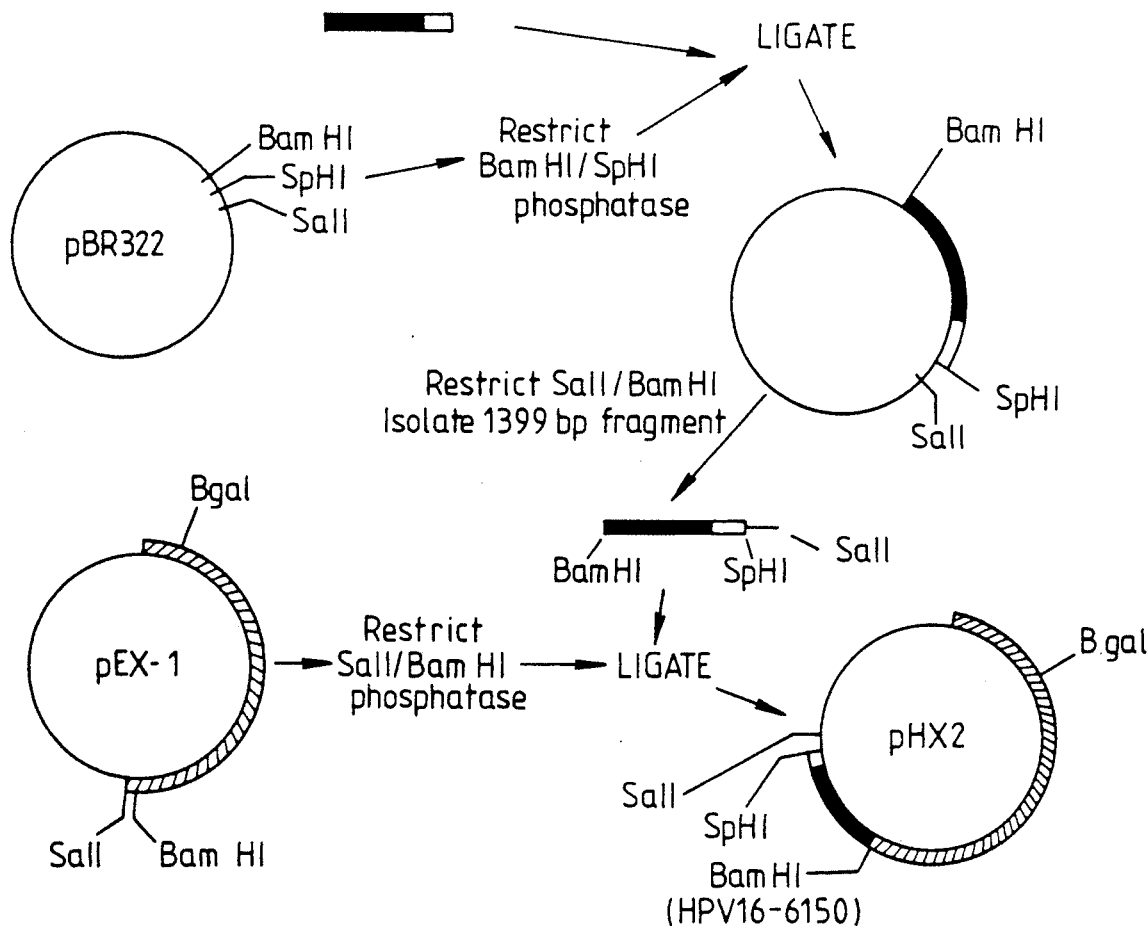

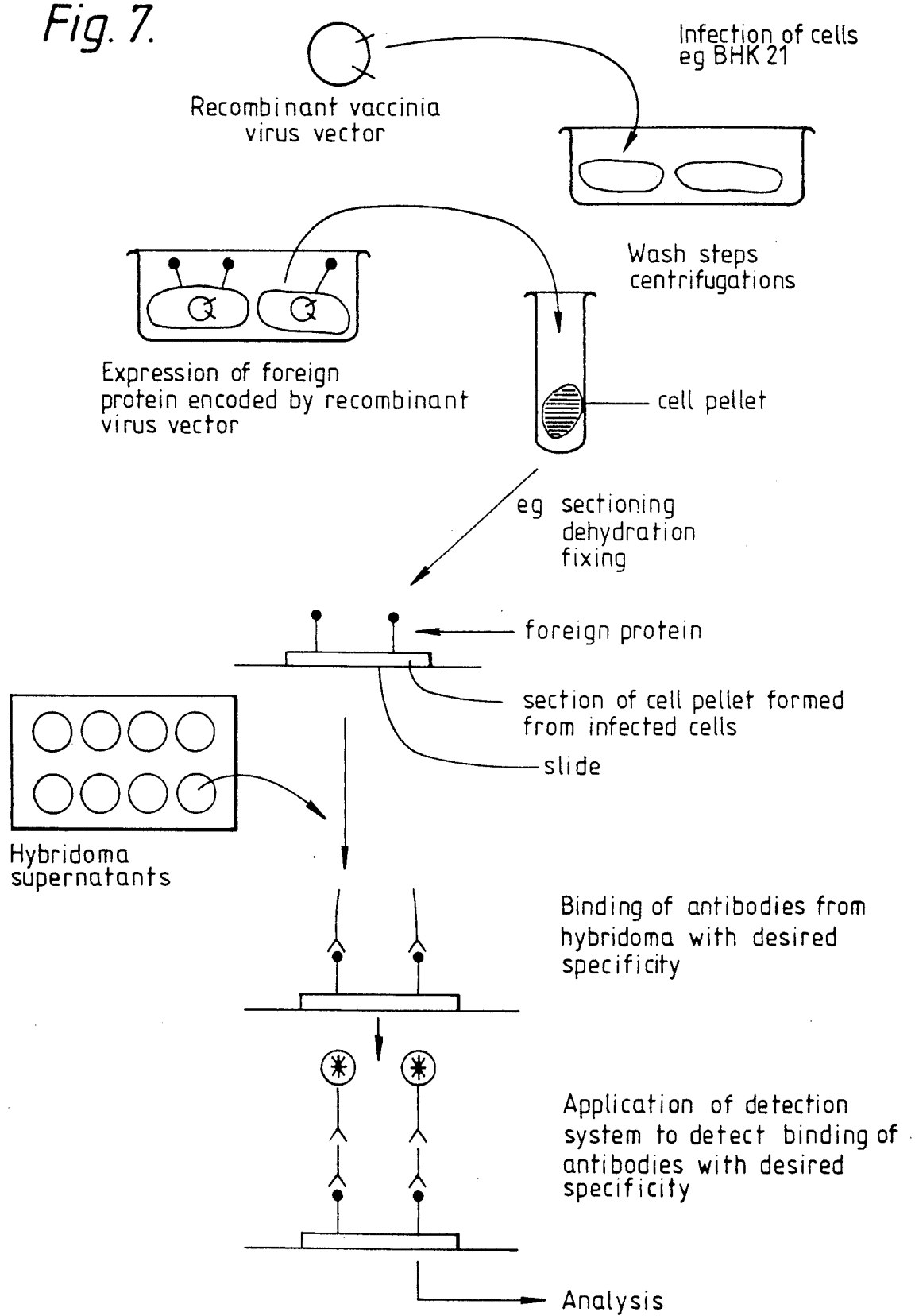

METHOD OF PRODUCING ANTIBODIES TO HPV

FIELD OF THE INVENTION

The present invention relates to a method for antibody production. In particular it relates to a method for producing monoclonal antibodies which are screened for their ability to bind to a specified antigen. The invention also relates to antibodies produced in this manner and to diagnostic procedures and kits utilizing such antibodies.

The present invention is exemplified herein, by way of example only, by the production of monoclonal antibodies to human papilloma virus (HPV), although it will be obvious to those skilled in the art that the techniques described may be usefully employed in many monoclonal antibody production systems.

BACKGROUND TO THE INVENTION

Human papilloma viruses are small (approximately 8 kb) DNA viruses and more than 40 types have now been reported as inducing epithelial or fibroepithelial proliferations of the skin or mucosa (zur Hausen, H., 1977, Current Topics in Microbiol. and Immunol. 78, 1-30). In particular the DNA of several HPV types is found in a variety of genital lesions, ranging from benign warts (both common and genital) which often contain HPV 6b or HPV 11 DNA (Gissmann L. et al, 1983, Proc. Nat. Acad. Sci. (USA) 80, 560-563), to invasive squamous cell carcinomas of the cervix, which frequently harbour HPV $-16$, $-18$, $-33$ or $-35$ genomes (Dürst M., et al 1983, Proc. Nat. Acad. Sci. USA 80, 3812-3815; Beaudenon S., et al 1986, Nature, Vol. 321, 246-249).

From the cytological examination of cervical smears it is possible to designate approximately 10% of the women from whom the smear samples were taken as being infected with HPV. Such women are then referred for further physical examinations, which frequently involve invasive diagnostic procedures. These further examinations usually reveal that of that 10%, most women are suffering from a non-serious HPV infection, whilst in a few, the forms of HPV infection will be more ominous. Thus in a screening system it would be useful to have a diagnostic test which both identifies HPV infection as being present, and distinguishes non-serious from serious HPV infection. In order to minimize equipment and training costs it would be advantageous for any new diagnostic test to utilize existing technology and slot easily into the present screening procedure. Furthermore, the provision of objective answers (rather than subjective assessments) by any such tests would allow automation, and this in turn would help to reduce both costs and waiting times, the latter being frequently stressful for the patients concerned.

To date no antibody-based clinical diagnostic tests are available for the detection of HPV infection. This is largely due to two problems. Firstly, it has not been possible to date to establish a permissive tissue culture system for the in vitro propagation of papilloma viruses. Secondly, clinical material is difficult to obtain, the viral proteins are usually present in only very small quantities in the clinical lesions, and the HPV causing the lesion is generally of unknown type. These two factors mean that a reliable and sufficient source of typed (i.e. known) HPV is not available for use as both an immunogen and screening agent in the large-scale production of monoclonal antibodies.

Up until now the production of antibodies to HPV (for research purposes) has been achieved using HPV proteins expressed in bacterial expression systems, or in the form of synthetic oligopeptides, as immunogens, and screening the hybridoma supernatants for antibodies produced against the immunogens by reusing the immunogens or various combinations thereof (Banks L., et al 1987, J. Gen. Virol. Vol 68, 3081-3089; Doorbar J. and Gallimore P., et al 1987, J. Virology 61, p. 2793-2799).

However, these known protocols for the production of monoclonal antibodies to HPV are generally unsuitable for the production of monoclonal antibodies which are to be used in immunocytochemical diagnostic tests for screening procedures. This is because antibodies produced by these protocols will not necessarily react with the naturally occurring HPV protein in infected human cells. In addition, the epitopes recognized by these antibodies will not necessarily be those epitopes which are resistant to the standard procedures involved in the sampling, fixing and storing of clinical specimens.

For successful use of an antibody in a diagnostic test the antibody must recognize an epitope which is common to the immunogen and the test sample as prepared for analysis (i.e. after any pre-treatment of tissues such as cryopreservation, sectioning and fixing). Therefore, the system chosen for screening large numbers of hybridoma culture supernatants must be such that it aids selection of diagnostically useful antibodies.

SUMMARY OF THE INVENTION

The invention provides an improved method of producing an antibody, wherein antibodies are screened for the ability to bind to a specified antigen; the improvement which comprises screening the antibodies with cells infected with a recombinant virus vector expressing an antigen specific for the desired antibody. Preferably, the antibodies are obtained from an animal which has been immunized with a protein expressed from recombinant DNA in suitable host organisms or with a synthetic oligopeptide, said protein or oligopeptide presenting an epitope homologous to an epitope encoded by the viral vector.

The term "homologous" in connection with epitopes is used to indicate that the epitopes are represented by substantially the same amino-acid sequence, while recognizing that because of their different manner of production they may not be identical in terms of their conformation. The process of the present invention enables antibodies to be identified which recognize common structural features of the homologous epitopes, and are therefore less likely to be affected by any conformational changes in the epitope presented by a prepared clinical sample. This latter feature can be further enhanced by screening the antibodies with the virally infected cells which have been prepared in a similar way to the preparation of clinical samples. Alternatively, antibodies obtained by the initial screening can be further screened against prepared clinical samples of known antigenicity (e.g. infected with HPV of known type), to ensure that the antibody has the required ability to recognize the epitope in that situation.

The invention also includes a diagnostic procedure in which an antibody is used to assay a clinical sample for the presence of a protein which presents an epitope to which the antibody is specific. The invention further includes a diagnostic kit which comprises an antibody, together with one or more reagents necessary for performing an assay on a clinical sample for the presence of a protein which presents an epitope to which the antibody is specific.

The method can be used for the production of antibodies which are able to distinguish between different strains of an immunogen. This may be achieved by screening the antibodies using cells infected with virus recombinants encoding one or more epitopes specific to a particular strain of immunogen. A suitable virus vector is vaccinia.

The method disclosed is particularly advantageous as: 1) cells infected with the virus recombinant can provide a good supply of an antigen; 2) the antigen is expressed in a mammalian cell and it is therefore synthesized and processed in a form essentially identical to the antigen found in a natural infection; and 3) the infected cells may be subjected to the same pre-treatments as applied to test sample tissues before their use in the hybridoma screening procedure. This ensures that the antibodies selected will recognize epitopes resistant to these pre-treatments and which may therefore be expected to be present on the test samples as prepared for analysis.

The recombinant virus infected cells can also be used in two other, but related, ways in conjunction with the antibody. One such use is in connection with obtaining the antibody. The infected cells can be used initially as a simple preparation, e.g. a monolayer culture, for the primary screening of the antibodies; and then the antibodies obtained in that way can be further screened using the virus-infected cells prepared in a manner appropriate to the preparation of clinical samples. Typically this latter would involve pelleting the infected cells by centrifugation, fixing, and preparing as a section. The fixing procedure would typically be by methanol where the clinical sample is to be a cervical smear, or formaldehyde/saline where the clinical sample is to be biopsy material.

Thus, prepared virally-infected cell material of this kind can be used generally for rescreening of antibodies, however they have been prepared initially. A preferred aspect of the present invention therefore comprises using cellular material from cells infected with a recombinant virus expressing a known antigen exogenous to the virus, to screen antibodies for binding to said antigen, said cellular material having been obtained by pelleting, fixing and sectioning in a manner appropriate to the preparation of clinical specimens for analysis.

The other related use of the virally-infected cells, which provides a further aspect of the invention, is in diagnostic kits using the antibody to assay a clinical sample, the kit including a specimen of the recombinant virus-infected cells, preferably prepared in a manner analogous to that used for clinical samples, so that it can provide a positive control for the assay.

Apart from papilloma virus, which provides problems as already indicated, the invention is applicable more generally, especially in relation to antibodies to virus which are difficult to grow in culture, and for antibodies to oncogene products which can likewise be expressed in cells from a recombinant virus, and indeed for antibodies to any antigen that is difficult to produce routinely in a native form.

A particular advantage of using virally infected cells as a screen or positive control, is that they can be prepared to present the antigen at known levels, for example equivalent to 1 cell in 10,000. Thus, one can judge, the suitability of an antibody for a particular assay, or the strength of a positive signal in the assay using the positive control.

BRIEF DESCRIPTION OF THE DRAWINGS

FIG. 1 shows the construction of an expression plasmid pHX2 for a fused $\beta$-galactosidase HPV16-L1 open reading frame;

FIG. 7 shows schematically the use of a screening system according to the present invention depicted in the form of a flow chart.

DETAILED DESCRIPTION OF THE PREFERRED EMBODIMENTS OF THE INVENTION

In order that the present invention may be more readily understood, an embodiment will now be described, by way of example only.

(1) Preparation of HPV-16 L1/$\beta$-galactosidase fusion protein (the immunogen)

A genomic clone of HPV-16 DNA was obtained (for details of the complete nucleotide sequence see Seedorf et al 1985, Virology 145, 181, incorporated herein by reference). A portion (amino acid 211 to C-terminus) of the HPV-16 L1 open reading frame was cloned as a Bam H1/Sph1 fragment (bases 6153-7464) from a genomic clone of HPV-16 DN and ligated into BamH1 and Sal1 sites of the vector pEx-1 (Stanley & Luzio 1984; EMBO J. 3, 1429, incorporated herein by reference), to yield a fused open reading frame of $\beta$-galactosidase and the C-terminal portion of HPV-16 L1. The resulting plasmid pHX2 was transfected into E.coli POP 2136 and heat induction resulted in the production of a $\beta$-gal fusion protein that was purified by gel electrophoresis. See FIG. No. 1

(2) Preparation of a recombinant vaccinia virus expressing the full length HPV-16 L1 protein (the screening target)

Figure 2:
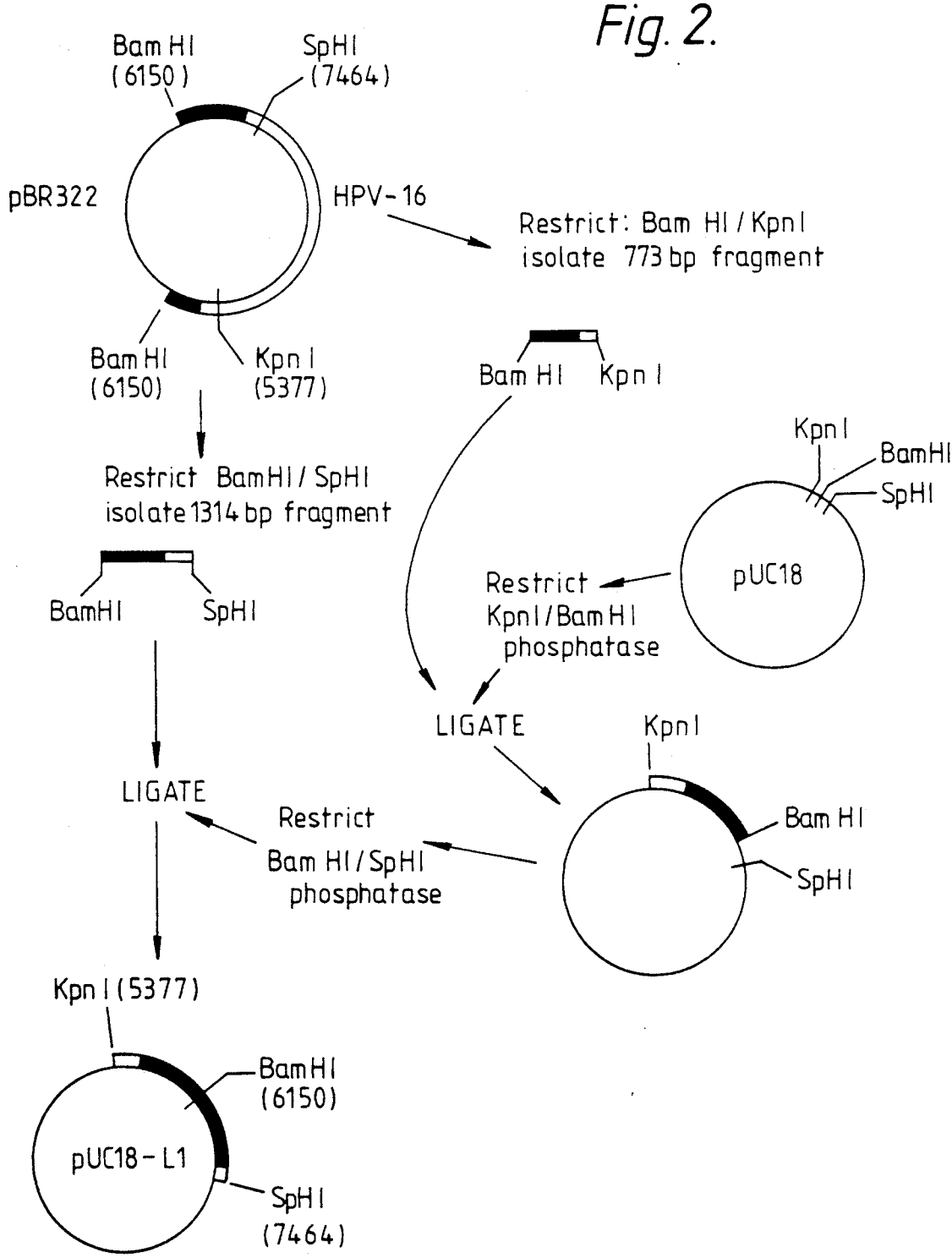
FIG. 2 shows the construction of a full length HPV16-L1 open reading frame in pUC18 (see also Browne, et al., *J. Gen. Virol.* 69, 1263 (1988)

The HPV-16 L1 open reading frame was introduced into the vector pUC18 in a Kpn1—Sph1 fragment (bases 5377-7464) derived from an HPV-16 genomic clone. See FIG. 2. The open reading frame was then excised from this vector in a 2074 bp fragment resulting from a partial EcoR1 digestion and this fragment was introduced into the EcoR1 site of pRK19, a vector containing a vaccinia late promoter (the promoter of the 4b late gene) flanked by vaccinia thymidine kinase coding sequences (R. Kent, Ph.D. thesis, Cambridge 1988 incorporated herein by reference but summarised below).

Figure 4:
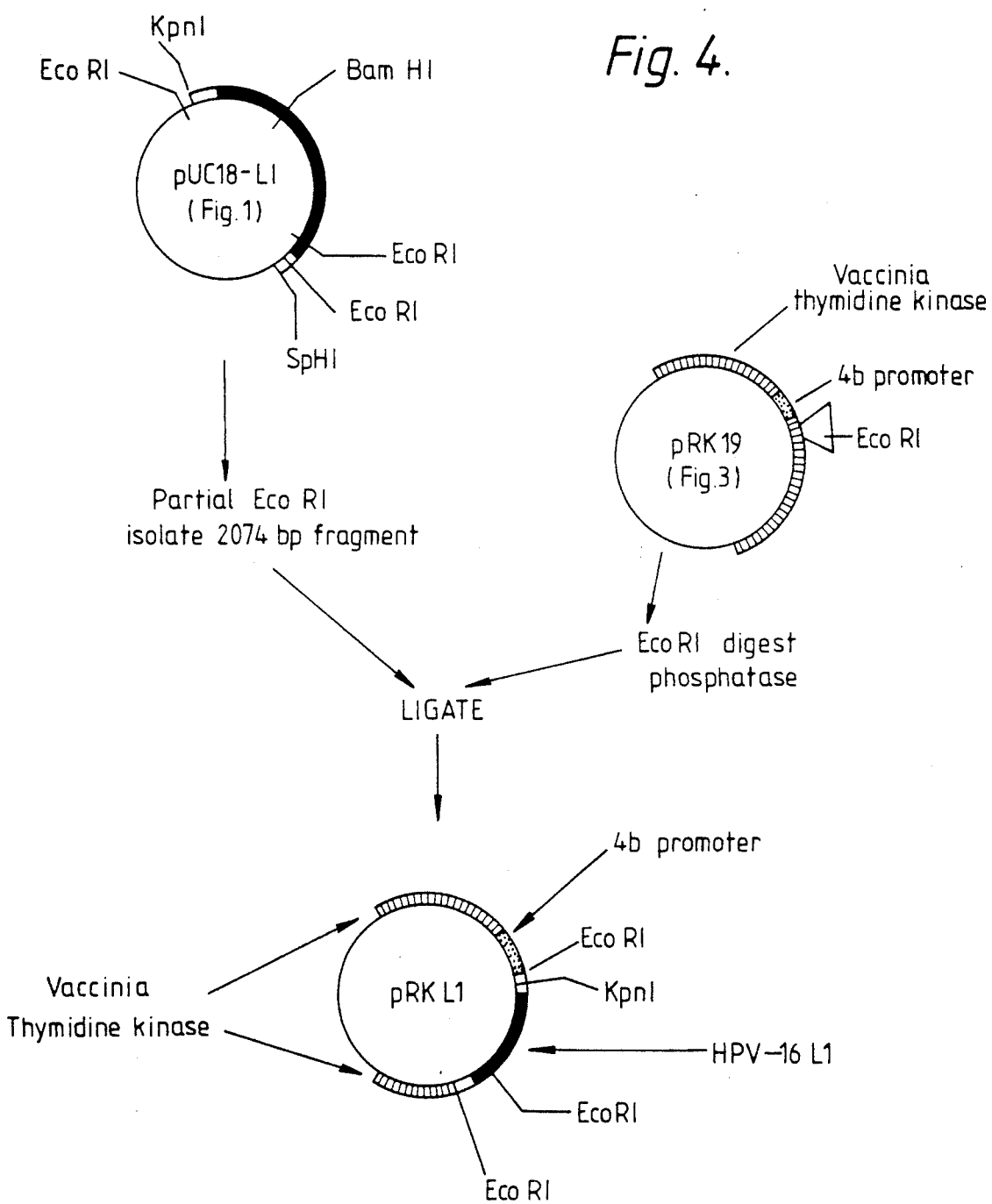
FIG. 4 shows the construction of an expression plasmid pRKL1 from pRK19, in which the PHV16-L1 gene is controlled by the vaccinia virus 4b promoter (see also Browne, et al., supra)

The resulting plasmid, pRKL1, contains the entire HPV-16 L1 gene under the control of the vaccinia late promoter. See FIG. 4. pRKL1 was transfected into CV-1 cells infected with wild-type vaccinia virus and recombinant viruses, lacking an intact thymidine kinase gene, were selected from the progeny by growth in 5-bromodeoxyuridine. Recombinant viruses were then identified by hybridization with a HPV-16 DNA probe and further characterised by restriction enzyme digestion. A recombinant virus containing the HPV-16 L1 gene inserted in the correct orientation was identified, and named vL1RK.

The procedures outlined in (1) and (2) above are described more fully in Browne et al 1988 J. Gen. Virol. 69, 1263-1273, incorporated herein by reference.

The steps in the construction of a plasmid containing the 4b gene promoter are as follows:

(a) The 4b gene coding sequence and 228 nucleotides of 5' sequence (containing the promoter and transcription start site) were isolated on a 2.3 kb Xba1 fragment derived from the vaccinia virus (WR strain) HIndIII A restriction fragment. The 2.3 kb Xba1 fragment was cloned into the Xba1 site of M13 mp19, and the majority of the 4b coding sequences were deleted by Xho1 cleavage, Bal 31 digestion and religation. The resulting insert in M13 mp19 contained 228 nucleotides of 'upstream' sequence and 31 nucleotides of 4b coding sequence.

(b) The remaining 4b coding sequences were deleted by site-directed mutagenesis so as to bring the cloning sites in M13 mp19 immediately 3' of the 4b promoter and transcription start site. The sequence in this region now reads

```
                          | Bam   Sma Kpn etc.
 . . . CGAATATAAATAA GGATCCCGGGTACC . . .
       Vaccinia 4b promoter  |     M13 mp19 cloning
             sequences       |          sites
```

Figure 3:
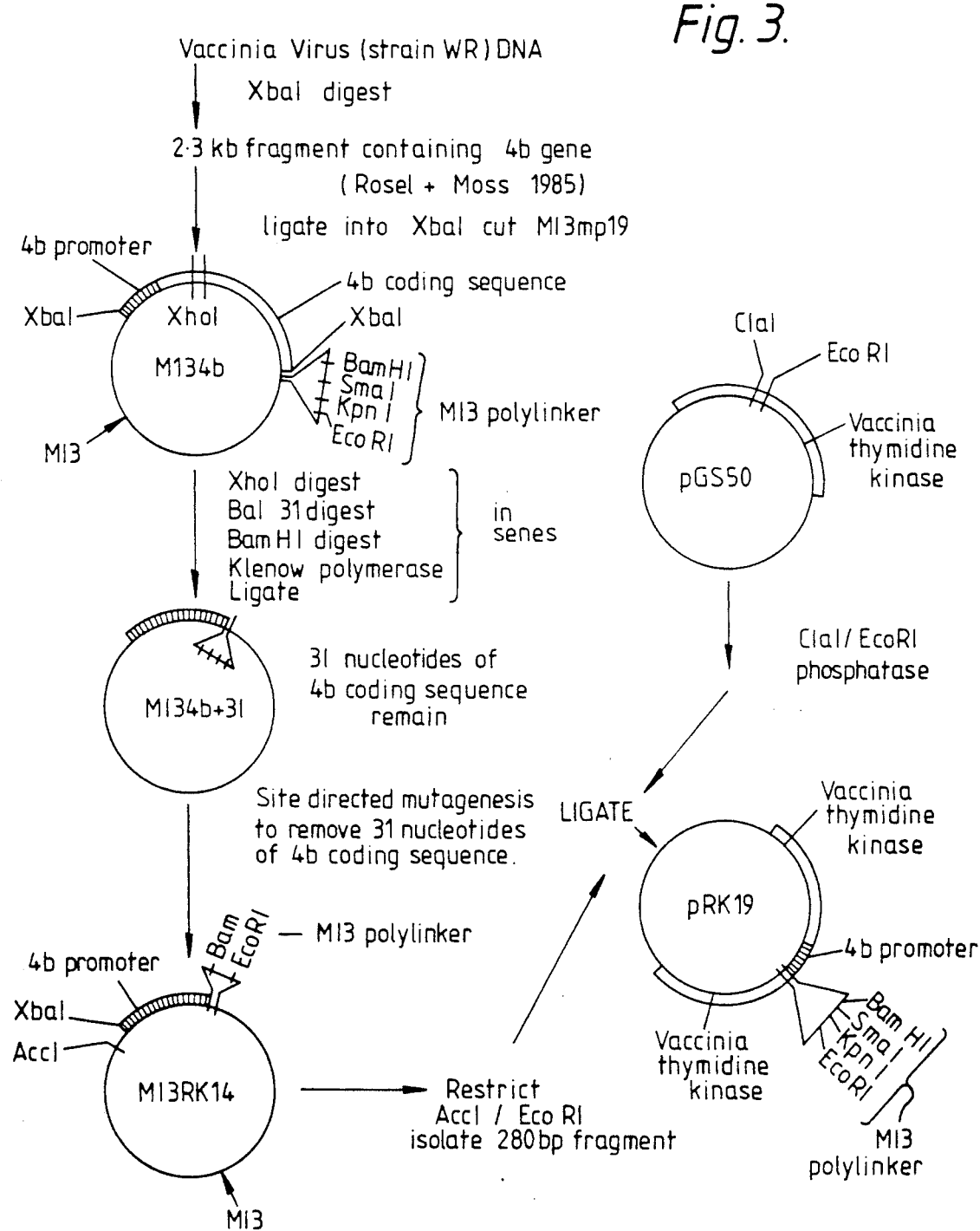
FIG. 3 shows the construction of a vaccinia expression plasmid pRK19, an insertion vector for expressing coding sequences under the control of the vaccinia virus 4b promoter.

Finally, pRK19 was constructed by removing these sequences from the vector (by EcoR1 and Acc1 digestion) and inserting them into the body of the vaccinia thymidine kinase gene in a vector analogous to pGS20 (see Mackett et al., 1984, Journal of Virology 49, 857, incorporated herein by reference). pRK19 thus has the properties given in FIG. 3.

This promoter was used because it was conveniently available, but in principle any of the vaccinia late promoters could have been used. The features of 'late' vaccinia promoters have been described by a number of groups e.g., Rosel et al. 1986, Journal of Virology 60, 436 and Betholet et al., 1986, EMBO Journal 5, 1951, both incorporated herein by reference. There are several examples of the use of these promoter sequences to drive the expression of foreign proteins in vaccinia virus recombinants e.g. Bertholet et al., 1984, PNAS 82, 2096 and Miner et al., 1988, Journal of Virology 62, 297, both incorporated herein by references and the vectors described by these authors would be suitable for expressing HPV coding sequences. The 4b gene promoter has the features typical of other 'late' promoters. The 4b gene and its promoter region have been sequenced by Rosel and Moss 1985, Journal of Virology 56, 830, incorporated herein by reference.

(3) Production of, monoclonal antibodies to HPV-16 L1

Mice were immunized with three intraperitoneal injections of 100 μg of the β-galactosidase-L1 fusion protein (prepared in (1) above), in incomplete Freunds adjuvant at monthly, intervals. Four days after the final immunization mouse spleen cells were fused with myeloma NSO cells and the fusion products were distributed among 48 × 1.5 cm diameter tissue culture wells. Culture supernatants were screened for HPV-16 L1-specific antibody by immunofluorescence assay using as a target BHK-21 fibroblasts infected with vLIRK as follows.

Monolayers of BHK-21 fibroblasts grown on glass slides were infected with recombinant vaccinia virus e.g. vL1RK at an MOI of 10 pfu-cell, and after 15 h at 37° C. the slides were fixed by immersion in 5% formaldehyde in phosphate-buffered saline (PBS) for 5 min. at room temperature. The slides were then washed in PBS. These fixed monolayers were then used as targets in antibody screening. Hybridoma culture supernatants were incubated on the fixed monolayers for 30 min at room temperature and, after washing in PBS, bound immunoglobulin was detected by incubation with fluorescein-conjugated rabbit anti-mouse IgG. A positive culture was identified on the basis of strong nuclear fluorescence and the cells in this culture were subjected to two rounds of limiting dilution cloning. The resulting hybridoma was named CAMVIR-1.

The secreted antibody was found to immunoprecipitate a protein of apparent Mr of about 55,000 from lysates of cells infected with vLIRK. This protein was not precipitated from lysates of cells infected with wild-type vaccinia virus. This apparent Mr was consistent with the predicted Mr of the HPV-16 L1 protein of about 53,000. The antibody was also found to give strong nuclear staining (using immunofluorescence and-/or immunoperoxidase staining) of cells infected with vLIRK and fixed with formaldehyde or methanol.

The potential diagnostic use of antibodies produced by hybridoma CAMVIR-1 in immunocytochemical screening procedures was investigated further. Cells infected with vL1RK were subjected to procedures equivalent to those routinely used on diagnostic samples of clinical biopsy material. The infected cells were pelleted by low speed centrifugation, the pellet fixed in formalin, dehydrated in an ethanol series, embedded in paraffin and then sectioned. The sections were dewaxed and subjected to immunoperoxidase staining (according to standard techniques known in the art) using monoclonal antibody CAMVIR-1. Strong nuclear staining was observed, indicating that these monoclonal antibodies recognize and bind epitopes expressed by cells infected with vL1RK, the expression of these epitopes not being destroyed by the procedures routinely applied to clinical samples.

The use of a recombinant vaccinia virus as a source of target antigen thus allowed the selection of an antibody with the required specificity, and allowed preliminary testing of the antibody to establish its likely usefulness for screening clinical material. The validity of these tests was subsequently confirmed by immunoperoxidase staining of clinical specimens. Antibody CAMVIR-1 detected HPV antigen in the cell nuclei of biopsy sections and cervical smear preparations known to be positive for HPV-16 (assessed by nucleic acid hybridization) but not in specimens known to be positive for HPV-6 or HPV-11.

(4) Production of monoclonal antibodies to HPV-16 E7

A similar approach was used to prepare two further hybridomas, CAMVIR-2 and -3 producing monoclonal antibodies against the E7 protein of HPV-16. Cloning and expression details for the HPV-16 E7 gene are as follows.

(a) Expression of a β-galactosidase-E7/β-galactosidase fusion protein (the immunogen)

Figure 5:
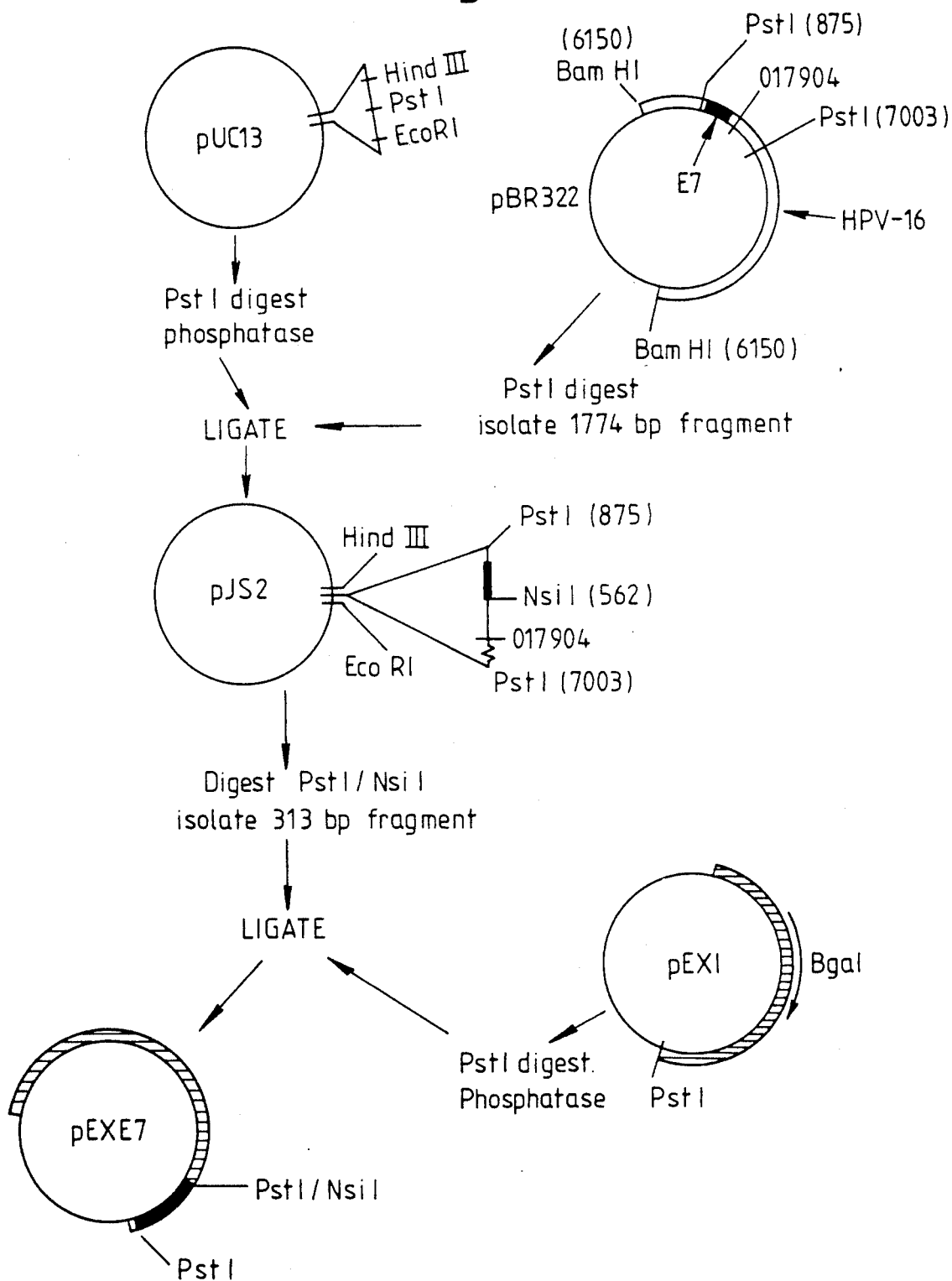
FIG. 5 shows the construction of an expression plasmid pEXE7 for a fused $\beta$-galactosidase HPV16-E7 open reading frame.

A genomic clone of HPV-16 (Seedorf et al, supra) was digested wit Pst1 and the resulting 1776 bp fragment (bases 7003-875), which includes the E7 open reading frame, was cloned into the Pst1 site of pUC13. The resulting plasmid pJS2 (see FIG. 5) was digested with Pst1 and Nsi1 and a 313 bp fragment (nucleotides 562-875) was cloned into the Pst1 site of pEx-1 (Stanley and Luzio, supra) to generate a fused β-galactosidase-E7 coding sequence pExE7. See FIG. 5. The expressed product was induced and the HPV-16 L1 fusion protein purified (See Browne et al, supra).

(b) Preparation of a recombinant vaccinia virus expressing HPV-16 E7 protein (the screening target)

Figure 6:
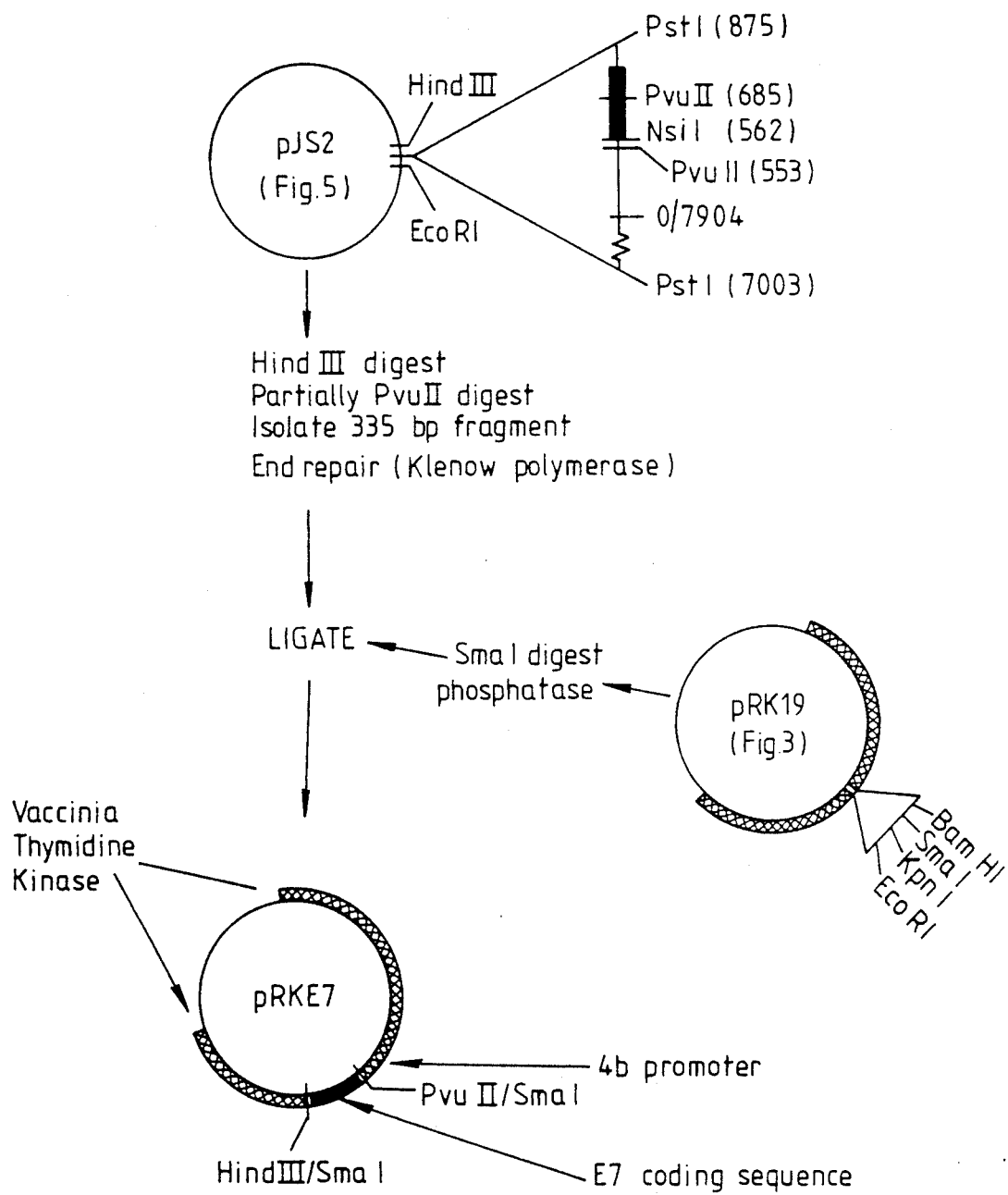
FIG. 6 shows the construction of an expression plasmid pRKE7 in which the HPV16-E7 gene is under the control of the vaccinia virus 4b promoter.

Plasmid pJS2 (FIG. 5) was linearized with HindIII and partially digested with PvuII. A 335 bp fragment originating from the pUC13 HindIII site and terminating at the HPV-16 PvuII site (nucleotide 553) was purified, end repaired and cloned into the SmaI site of pRK19 (see FIG. 2) such that the E7 gene is expressed under the control of the vaccinia 4b late promoter pRKE7. See FIG. 6. Transfection of CV-1 cells and isolation of a recombinant, thymidine kinase negative virus, was as described for the production of an L1-recombinant (Mackett et al, supra).

(c) Production of the HPV-16 E7 monoclonal antibodies

The β-galactosidase-E7 fusion, protein (prepared in (a) above) was used to immunize mice as described for the HPV-16 L1 fusion protein, followed by the other procedures set forth in Part (3) above to provide CAMVIR-2 and -3. See the first sentence introduction of this part (4).

The methods exemplified above are generally applicable to other antigens, and to the use of other viral vectors.

I claim:

1. In a method of producing an antibody, wherein antibodies are screened for the ability to bind to a specified antigen; the improvement which comprises screening the antibodies with intact fixed or unfixed cells infected with a recombinant virus vector expressing an antigen specific for the desired antibody, which antigen is a polypeptide comprising an epitope of human papilloma virus (HPV).

2. The improved method of claim 1, wherein the virus vector is vaccinia.

3. The improved method of claim 1, wherein the epitope is comprised in the HPV-16 L1 protein or HPV-16 E7 protein.

4. The improved method of claim 1 wherein the antibodies are obtained from an animal which has been immunized with a protein expressed from recombinant DNA in a suitable host organism or with a synthetic oligopeptide, said protein or oligopeptide presenting an epitope homologous to an epitope encoded by the viral vector.

5. The improved method of claim 1 wherein the virally infected cells used for screening are first subjected to one or more procedures conventional for the preparation of clinical samples to be assayed for the presence of said epitope.

6. The improved method of claim 1 wherein antibodies selected by said screening procedure are then subjected to further screening against one or more prepared clinical samples known to contain the protein from which said epitope is derived.

7. The improved method of claim 1 wherein antibodies are subjected to a first screening procedure with said virally infected cells, and the antibodies thus obtained are subjected to a second screening procedure with said virally infected cells, the cells in said second screening having been prepared in a manner analogous to that used for preparing clinical samples for analysis.

8. A diagnostic procedure comprising incubating an antibody produced by the method of claim 1 with a clinical sample and measuring the immunocrossreactivity of said antibody with any protein which presents an epitope to which the antibody is immunospecific.

9. A diagnostic kit which comprises an antibody of claim 1, together with one or more reagents necessary to assay a clinical sample for the presence of an epitope to which the antibody is specific.

10. In a diagnostic kit comprising an antibody specific to a target antigen in a clinical sample together with one or more reagents necessary for performing the assay, the improvement which comprises the provision of a positive control in the form of a specimen of cells infected with a recombinant virus expressing an antigen homologous to the target antigen, which antigen is a polypeptide comprising an epitope of human papilloma virus (HPV).

11. The improved diagnostic kit of claim 10, wherein said positive control specimen has been prepared in a manner analogous to that required for the clinical sample suspected of containing the antigen.

12. The improved kit of claim 11 wherein the preparation of said positive control specimen includes pelleting, fixing and sectioning the cells.

13. A diagnostic kit which comprises:
 (i) an antibody specific for a given antigen which is a polypeptide comprising an epitope of human papilloma virus (HPV);
 (ii) reagents for using that antibody to detect an analyte in a clinical sample;
 (iii) a positive control specimen comprising cells infected with a recombinant viral vector expressing said antigen;
 (iv) reagents for detecting the binding of said antibody (i) with the antigen in the specimen (iii).

14. A diagnostic kit according to claim 13, wherein reagents (iv) are included in reagents (ii).

15. A diagnostic kit according to claim 13 wherein the specimen (iii) is fixed in a manner analogous to that appropriate for the clinical sample.

16. A diagnostic kit according to claim 15 wherein the positive control specimen (iii) is prepared by pelleting, fixing and sectioning the cells and presenting the section on a slide.

17. A diagnostic kit according to claim 13 wherein the positive control specimen (iii) has a known level of expression of the antigen and/or a known proportion of cells expressing the antigen.

* * * * *